United States Patent
Brenneman et al.

(10) Patent No.: US 8,906,305 B2
(45) Date of Patent: Dec. 9, 2014

(54) ANALYTE-TESTING INSTRUMENTS

(75) Inventors: Allen J. Brenneman, Goshen, IN (US); Huan-Ping Wu, Granger, IN (US)

(73) Assignee: Bayer HealthCare LLC, Whippany, NJ (US)

( * ) Notice: Subject to any disclaimer, the term of this patent is extended or adjusted under 35 U.S.C. 154(b) by 0 days.

(21) Appl. No.: 12/530,669

(22) PCT Filed: Mar. 12, 2007

(86) PCT No.: PCT/US2007/006231
§ 371 (c)(1),
(2), (4) Date: Sep. 10, 2009

(87) PCT Pub. No.: WO2008/111937
PCT Pub. Date: Sep. 18, 2008

(65) Prior Publication Data
US 2010/0041156 A1 Feb. 18, 2010

(51) Int. Cl.
*G01N 35/00* (2006.01)
*B65D 83/00* (2006.01)
*G01N 33/487* (2006.01)
G01N 33/50 (2006.01)
G01N 33/66 (2006.01)
B65D 83/08 (2006.01)
G01N 33/49 (2006.01)

(52) U.S. Cl.
CPC .......... *G01N 33/48785* (2013.01); *G01N 33/49* (2013.01); *G01N 33/48757* (2013.01); *B65D 83/00* (2013.01); *G01N 33/4875* (2013.01); *G01N 2035/00089* (2013.01)
USPC .......... 422/68.1; 422/82.01; 436/95; 221/92; 221/97; 221/102

(58) Field of Classification Search
CPC .................... G01N 33/48757; G01N 33/4875; G01N 2035/00089
See application file for complete search history.

(56) References Cited

U.S. PATENT DOCUMENTS 3,393,795 A    7/1968    Covert
3,876,269 A    4/1975    Fisher et al.
(Continued)

FOREIGN PATENT DOCUMENTS

DE    102004057503    6/2006
EP    1285695    2/2003
(Continued)

OTHER PUBLICATIONS

Papadea, C. et al. "Evaluation of the i-STAT Portable Clinical Analyzer for Point-of-Care Blood Testing in the Intensive Care Units of a University Children's Hospital," Annals of Clinical & Laboratory Science 2002, 32, 231-243.*

(Continued)

*Primary Examiner* — Yelena G Gakh
*Assistant Examiner* — Michelle Adams
(74) *Attorney, Agent, or Firm* — Nixon Peabody LLP (57) ABSTRACT

An instrument adapted to determine an analyte concentration of a fluid sample using a test sensor is disclosed. The instrument comprises a display adapted to display information to a user, a user-interface mechanism adapted to allow the user to interact with the instrument, a first test-sensor cartridge, and a body portion including at least a first opening and a second opening formed therein. The first opening is adapted to receive a test sensor from the first test-sensor cartridge. The second opening is adapted to store at least one additional test-sensor cartridge.

12 Claims, 6 Drawing Sheets

(56) References Cited

U.S. PATENT DOCUMENTS

| | | | |
|---|---|---|---|
| 4,197,287 A | 4/1980 | Piasio et al. | |
| 5,510,266 A | 4/1996 | Bonner et al. | |
| 5,575,403 A | 11/1996 | Charlton et al. | |
| 5,632,410 A | 5/1997 | Moulton et al. | |
| 5,645,798 A | 7/1997 | Schreiber et al. | |
| 5,660,791 A | 8/1997 | Brenneman et al. | |
| 5,720,924 A | 2/1998 | Eikmeier et al. | |
| 5,863,800 A | 1/1999 | Eikmeier et al. | |
| 5,875,897 A | 3/1999 | Duncan et al. | |
| 6,062,420 A | 5/2000 | Krouwel et al. | |
| 6,497,845 B1 | 12/2002 | Sacherer | |
| 6,540,672 B1 | 4/2003 | Simonsen | |
| 6,595,365 B1 | 7/2003 | Wigmore | |
| 2003/0059350 A1 | 3/2003 | Sacherer | |
| 2003/0089730 A1 | 5/2003 | May | |
| 2003/0199901 A1* | 10/2003 | Boecker et al. | 606/181 |
| 2003/0212345 A1* | 11/2003 | McAllister et al. | 600/584 |
| 2004/0009100 A1* | 1/2004 | Simons et al. | 422/102 |
| 2004/0047764 A1 | 3/2004 | Purcell | |
| 2004/0055898 A1 | 3/2004 | Heller et al. | |
| 2004/0092995 A1 | 5/2004 | Boecker et al. | |
| 2004/0094564 A1 | 5/2004 | Papp | |
| 2004/0230216 A1 | 11/2004 | Levaughn et al. | |
| 2005/0027211 A1 | 2/2005 | Kuhr et al. | |
| 2005/0153428 A1 | 7/2005 | Matsumoto | |
| 2005/0187444 A1 | 8/2005 | Hubner et al. | |
| 2006/0184065 A1 | 8/2006 | Deshmukh et al. | |
| 2006/0241666 A1 | 10/2006 | Briggs et al. | |
| 2006/0275890 A1 | 12/2006 | Neel | |
| 2006/0276724 A1 | 12/2006 | Freeman et al. | |
| 2009/0162248 A1* | 6/2009 | Creaven et al. | 422/68.1 |

FOREIGN PATENT DOCUMENTS

| | | |
|---|---|---|
| EP | 1475038 | 11/2004 |
| EP | 1475630 | 11/2004 |
| JP | 2002196003 | 7/2002 |
| WO | WO 2005/065828 | 7/2005 |
| WO | WO 2006/035322 | 4/2006 |

OTHER PUBLICATIONS

Written Opinion of the International Searching Authority corresponding to co-pending International Patent Application No. PCT/US2007/006231, European Patent Office, dated Apr. 9, 2008, 9 pages.

International Search Report corresponding to co-pending International Patent Application No. PCT/US2007/006231, European Patent Office, dated Apr. 9, 2008, 6 pages.

* cited by examiner

ANALYTE-TESTING INSTRUMENTS

CROSS-REFERENCE TO RELATED APPLICATION

This application is a nationalized application of PCT/US2007/006231 filed on Mar. 12, 2007.

FIELD OF THE INVENTION

The present invention relates generally to analyte-testing instruments and, more particularly, to analyte-testing instruments including one or more compact test-sensor cartridges and mechanisms for indexing and/or excising test sensors from the test-sensor cartridge.

BACKGROUND OF THE INVENTION

The quantitative determination of analytes in body fluids is of great importance in the diagnoses and maintenance of certain physiological abnormalities. For example, lactate, cholesterol, and bilirubin should be monitored in certain individuals. In particular, determining glucose in body fluids is important to diabetic individuals who must frequently check the glucose level in their body fluids to regulate the glucose intake in their diets. The results of such tests may be used to determine what, if any, insulin and/or other medication needs to be administered. In one type of testing system, test sensors are used to test a fluid such as a sample of blood.

One method of monitoring an individual's blood glucose level is with a portable, hand-held blood glucose testing device (e.g., a meter). To determine the blood glucose level with the meter, a lancet device may be used with a needle lancet that pierces the skin tissue and allows a whole blood sample to form on the skin's surface. Once the requisite amount of blood forms on the skin's surface, the blood sample is transferred to a test sensor. The test sensor is generally placed in an opening in the body of the meter.

Test-sensor cartridges are commonly used to individually dispense test sensors to be used for testing an analyte in a fluid. Test-sensor cartridges may be incorporated directly into, for example, glucose meters to dispense test sensors for use with the meter. The cartridges are used to store multiple sensors and allow users to carry multiple sensors around within a single enclosure. The cartridges also assist in preventing or inhibiting the sensors from being exposed to the environment until they are required for use. A blood or body fluid sample may then be placed on the sensor and analyzed with the meter or similar device to determine the concentration of the analyte being examined.

Each time analyte-testing is performed, a new test sensor is used, and thus, a number of test sensors may be used in a single day. Existing meters are adapted to include, at most, one test-sensor cartridge. This may be undesirable since a user may realize that he or she has used all of the test sensors in the test-sensor cartridge at inopportune times. For example, the user may run out of test sensors while away from home and without having an extra cartridge available, thereby potentially causing substantial inconvenience to the user.

Typically, a meter includes some type of mechanism for indexing and/or excising each test sensor from a cartridge. To index a cartridge, the cartridge may be rotated so that an empty test-sensor cavity may be removed from an excise position and replaced with a test-sensor cavity having a next test sensor therein. The next test sensor may then be excised from the cartridge for use in testing a desired analyte. Indexing and/or excising mechanisms are often complex. For example, the indexing and/or excising mechanism may be motorized. Such a complex indexing and/or excising mechanism may be undesirable since often, many different parts are required, which may increase the cost of manufacturing. Moreover, complex mechanisms may be particularly susceptible to breakage, thus requiring repair or replacement.

It would be desirable to have analyte-testing instruments that assist in addressing one or more of the above disadvantages.

SUMMARY OF THE INVENTION

According to one embodiment of the present invention, an instrument adapted to determine an analyte concentration of a fluid sample using a test sensor is disclosed. The instrument comprises a display adapted to display information to a user, a user-interface mechanism adapted to allow the user to interact with the instrument, a first test-sensor cartridge, and a body portion including at least a first opening and a second opening formed therein. The first opening is adapted to receive a test sensor from the first test-sensor cartridge. The second opening is adapted to store at least one additional test-sensor cartridge.

According to another embodiment of the present invention, a mechanism adapted to index and excise a test sensor from a test-sensor cartridge is disclosed. The mechanism comprises an indexer comprising an indexer face, a retention pin, a flexible pawl, and a user-accessible tab. The retention pin extends through a first aperture formed generally through the center of the indexer face. The indexer is adapted to be rotated in a first direction and a second direction about the retention pin. The flexible pawl is positioned near an edge of the indexer face. The flexible pawl is adapted to assist in rotating the test-sensor cartridge. The indexer face forms a second aperture therein. The second aperture is adapted to be generally aligned with the test sensor. The mechanism further comprises an excise mechanism comprising a push rod adapted to extend through the second aperture and a bar coupled with and generally parallel to the push rod.

According to another embodiment of the present invention, an analyte-testing instrument adapted to determine the concentration of at least one analyte in a fluid is disclosed. The analyte-testing instrument comprises a display adapted to display information to a user, a user-interface mechanism adapted to allow the user to interact with the instrument, and a body portion including at least one opening formed therein, the at least one opening being adapted to receive a test sensor. The instrument further comprises an indexer positioned within the body portion. The indexer comprises an indexer face, a retention pin, a flexible pawl, and a user-accessible tab. The retention pin extends through a first aperture formed generally through the center of the indexer face. The indexer is adapted to be rotated in a first direction and a second direction about the retention pin. The flexible pawl is positioned near an edge of the indexer face. The flexible pawl is adapted to assist in rotating the test-sensor cartridge. The indexer face forms a second aperture therein. The second aperture is adapted to be generally aligned with the test sensor. The instrument further comprises an excise mechanism positioned within the body portion. The excise mechanism comprises a push rod adapted to extend through the second aperture and a bar coupled with and generally parallel to the push rod.

According to another embodiment of the present invention, a method of indexing and excising a test sensor from a test-sensor cartridge is disclosed. The method comprises the act of providing a test-sensor cartridge comprising a first face, a second opposing face, and a side portion connecting the first and second opposing faces, the first face forming a plurality of test-sensor cavities that is generally uniformly positioned therethrough, and a plurality of generally uniformly spaced notches positioned on an end of the cartridge opposite the cartridge face, the number of notches corresponding to the number of cavities. The method further comprises the act of providing an indexer comprising an indexer face, a retention pin extending through a first aperture formed generally through the center of the indexer face, a second aperture formed on the indexer face, a flexible pawl positioned near an edge of the indexer face, the flexible pawl being adapted to assist in rotating the test-sensor cartridge, and a user-accessible tab. The method further comprises the act of providing an excise mechanism comprising a push rod adapted to extend through the second aperture and a bar coupled with and generally parallel to the push rod. The method further comprises the act of rotating the indexer in a first direction about the retention pin such that the flexible pawl is positioned between a first notch and an adjacent second notch. The notches are set off at an angle such that rotating the indexer in a first direction, but not in a second generally opposite direction, likewise rotates the cartridge. The method further comprises the act of rotating the indexer in the second direction such that the flexible pawl is positioned between the second notch and an adjacent third notch and the second aperture is generally aligned with a first test-sensor cavity. The method further comprises the act of moving the excise mechanism in a lateral direction such that the push rod extends through the second aperture and through a first end of the first test-sensor cavity. The method further comprises the act of continuing to move the excise mechanism in the lateral direction until the first test sensor is excised through the second end of the first test-sensor cavity into a read position.

The above summary of the present invention is not intended to represent each embodiment or every aspect of the present invention. Additional features and benefits of the present invention are apparent from the detailed description and figures set forth below.

BRIEF DESCRIPTION OF THE DRAWINGS

FIG. 3b is a side perspective view of the test-sensor cartridge of FIG. 3a.

FIG. 4b is a detailed perspective view of the mechanism of FIG. 4a.

DESCRIPTION OF ILLUSTRATED EMBODIMENTS

The present invention is directed to analyte-testing instruments including one or more compact test-sensor cartridges and mechanisms for indexing and/or excising a test sensor from a test-sensor cartridge. The test sensors (e.g., biosensors) excised from the cartridge may be used to assist in determining an analyte concentration in a fluid sample. Some examples of the types of analytes that may be collected and analyzed include glucose, lipid profiles (e.g., cholesterol, triglycerides, LDL, and HDL), microalbumin, fructose, lactate, or bilirubin. The present invention is not limited, however, to these specific analytes, and it is contemplated that other analyte concentrations may be determined. The analytes may be in, for example, a whole blood sample, a blood serum sample, a blood plasma sample, or other body fluids like ISF (interstitial fluid) and/or urine. One non-limiting example of the analyte-testing instruments' use is to determine the glucose concentration in a user's blood, plasma, or ISF.

Figure 1A:
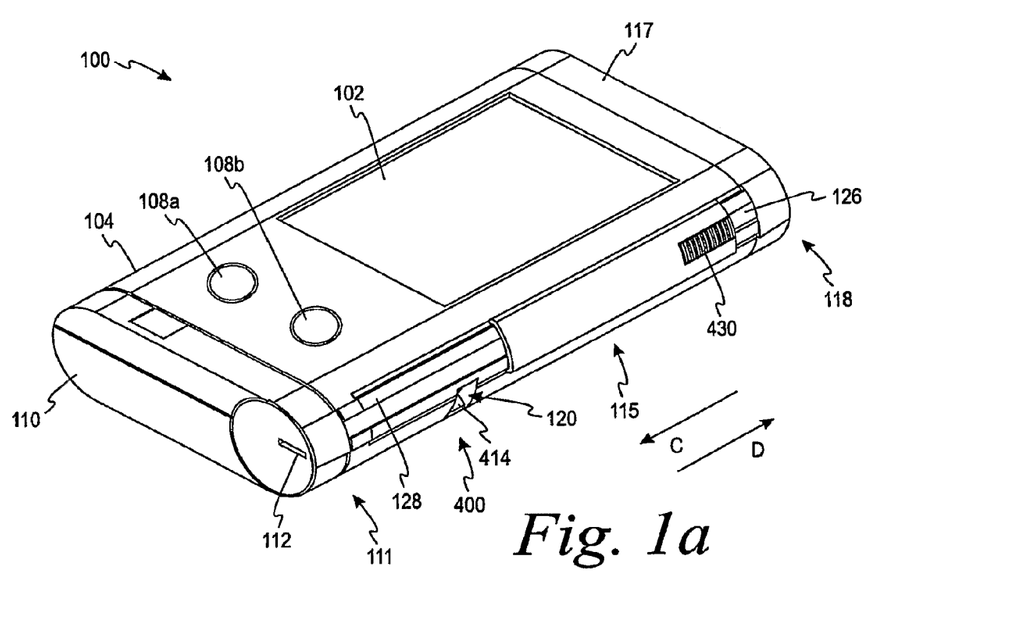
FIG. 1a is a top perspective view of a meter according to one embodiment of the present invention.
Figure 1B:
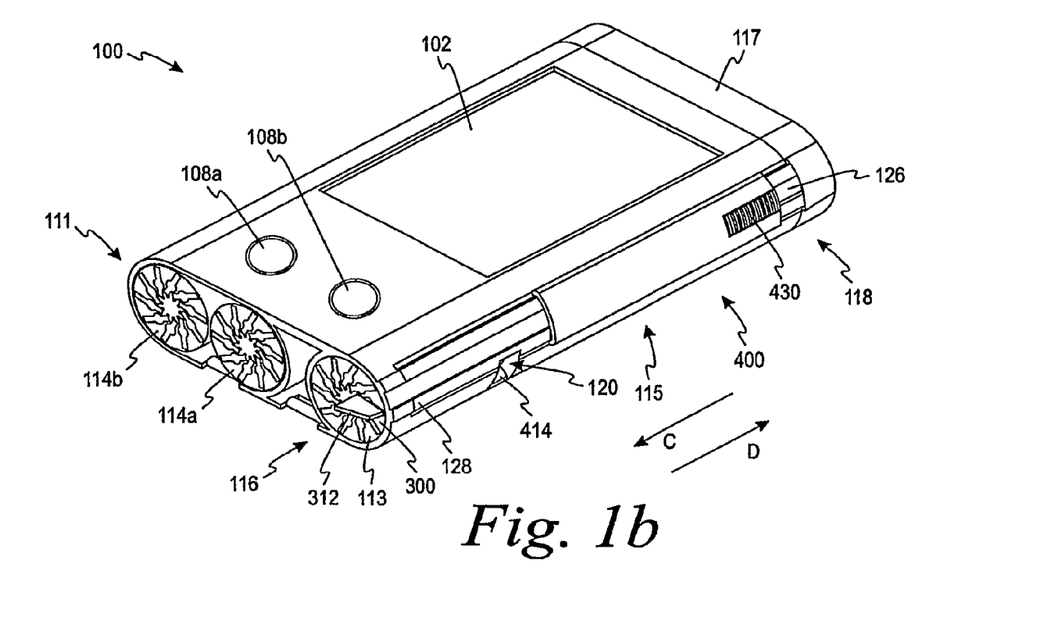
FIG. 1b is a top perspective view of the meter of FIG. 1a without a cover.
Figure 1C:
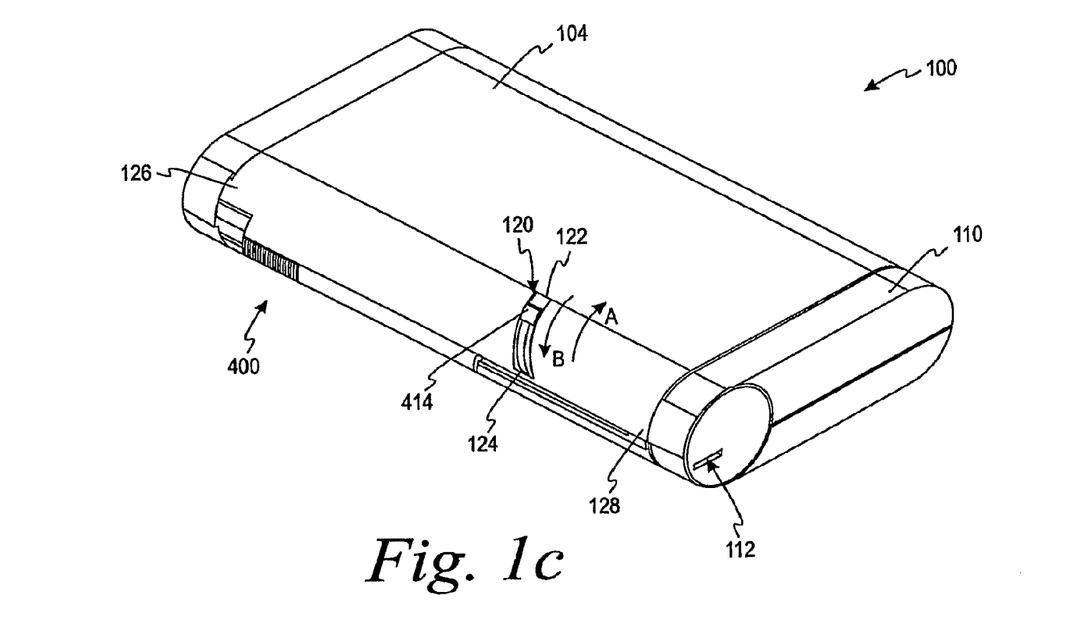
FIG. 1c is a bottom perspective view of the meter of FIGS. 1a,b.

Turning now to the drawings and initially to FIGS. 1a-c, an analyte-testing instrument or meter 100 is shown according to an embodiment of the present invention. The meter 100 includes a display 102, a body portion 104, and a user-interface mechanism. In the embodiment of FIGS. 1a-c, the user-interface mechanism includes a plurality of buttons 108a,b. It is contemplated that a different number of buttons 108a,b may be included on the meter 100. The buttons may also have a different shape, size, and/or position on the meter 100 than the buttons 108a,b shown in FIGS. 1a-c. It is also contemplated that the user-interface mechanism may include other mechanisms suitable for communicating with the meter 100 including, but not limited to, a scroll wheel and/or a touch screen. One example of a display 102 that may be used in the meter 100 is a liquid-crystal display. The meter 100 typically shows information from a testing procedure and/or in response to signals input by the user-interface mechanism (e.g., buttons 108a,b) on the display 102 and then stores the information in memory. The result of the testing may also be announced audibly, by, for example, using a speaker, and stored in memory.

The body portion 104 of meter 100 further includes a protective cover 110 (FIG. 1a) that is at least partially removably coupled to a first end 111 of the meter 100. The cover 110 forms a test-sensor dispensing port 112 extending therethrough. The test-sensor dispensing port 112 is adapted to receive and/or hold a test sensor. The cover 110 may be coupled to the meter 100 by any suitable means including, for example, a snap-fit method, a hinge, a latch, a living hinge, or combinations thereof. FIG. 1b shows the meter 100 after the cover 110 has been removed. Upon removing the cover 110, at least one test-sensor cartridge 300, 114a,b housed within the meter 100 is exposed and may be accessed.

According to one embodiment of the present invention, the meter 100 is adapted to house more than one test-sensor cartridge 300, 114a,b. Storing replacement test-sensor cartridges within a meter may be desirable so that a user may carry multiple cartridges around within a single enclosure. Moreover, once the user places the replacement cartridges in the meter, the user need not concern him or herself with whether a presently in-use cartridge includes an adequate amount of unused test sensors or with remembering to bring an extra cartridge, for example, each time the user leaves the house.

Typically, a cartridge 300 may be positioned such that an individual test sensor within the cartridge 300 may be excised from the cartridge 300 for use in analyte-testing. In the illustrated embodiment, the cartridge 300 is positioned adjacent to a semicircular end 115 of the meter 100 such that the cartridge 300 is generally located at a corner 116 of the meter 100. It is contemplated that the semicircular end 115 may have other shapes such as, for example, polygonal. At least one replacement cartridge 114a,b may be stored in other compartments of the meter 100 for future use. In the embodiment of FIG. 1b, the replacement cartridges 114a,b are accessible from the first end 111 of the meter 100 adjacent to the cartridge 300 and are adapted to be protected from contaminants by the cover 110. Although the meter 100 of the illustrated embodiment includes two replacement cartridges 114a,b, it is contemplated that a different number of replacement cartridges may be stored within the meter 100 such as, for example, one or at least three replacement cartridges.

Alternatively or additionally, the meter 100 may include a second removable cover 117 positioned on a second end 118 of the meter 100 and adapted to store additional replacement cartridges. It is contemplated that the replacement cartridges 114a,b may be stacked within the meter 100. It is also contemplated that the replacement cartridges 114a,b may be stored in a compartment of the meter 100 other than those shown in FIGS. 1a-c and described above.

Figure 2A:
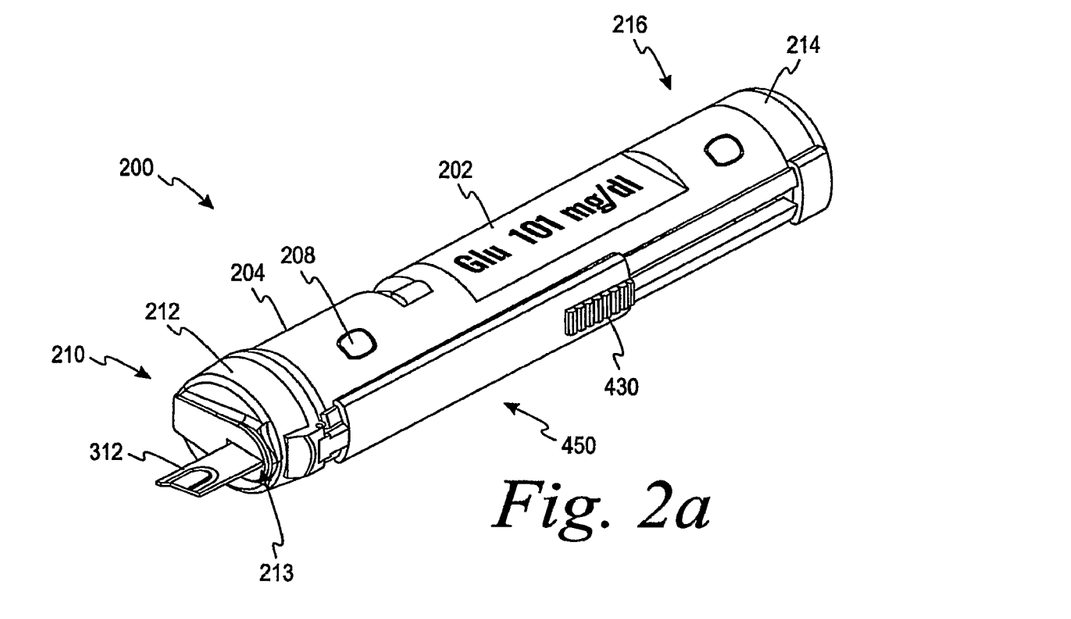
FIG. 2a is a top perspective view of a meter according to another embodiment of the present invention.
Figure 2B:
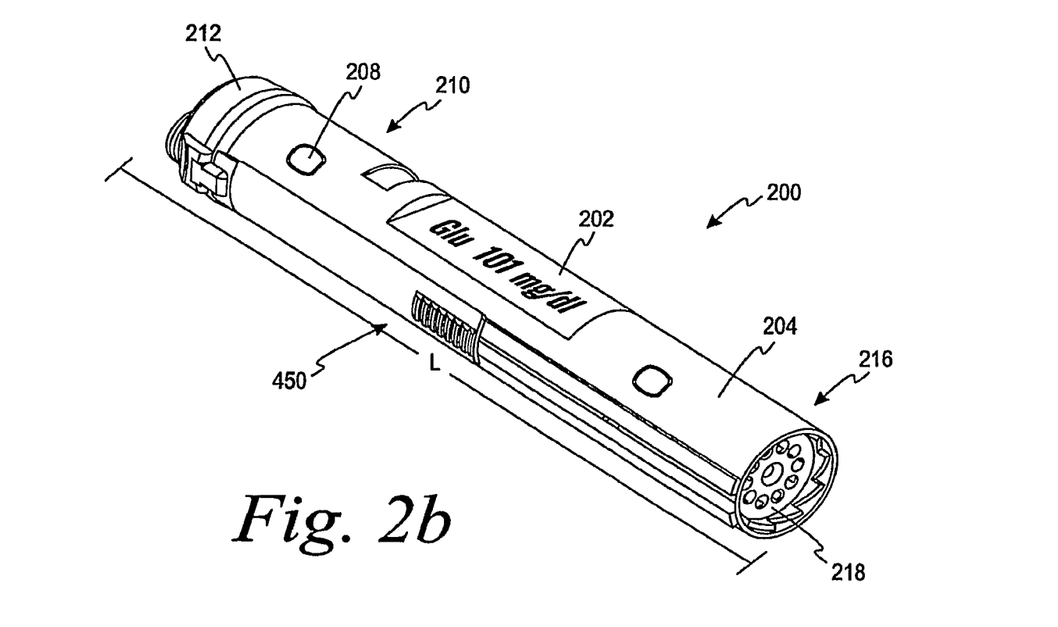
FIG. 2b is a top perspective view of the meter of FIG. 2a without a cover.

It is contemplated that a meter other than that illustrated in FIGS. 1a-c may be used with the present invention. For example, FIGS. 2a,b show an instrument or a pen meter 200 according to another embodiment. The pen meter 200 of FIGS. 2a,b is generally round in shape and includes a display 202, a body portion 204, and a user-interface mechanism 208. It is contemplated that the pen meter 200 may have other shapes such as, for example, polygonal (e.g., octagon, nonagon, decagon). The pen meter 200 of FIGS. 2a,b may further include a test-sensor cartridge (not shown) positioned at a first end 210 of the pen meter 200 such that an individual test sensor may be excised from the test-sensor cartridge for use in analyte-testing. The test-sensor cartridge is enclosed by a protective cover 212 at least partially removably coupled to the first end 210. The cover 212 may be coupled to the pen meter 200 by any suitable means including, for example, a snap-fit method, a hinge, a latch, a living hinge, a threaded screw or fastener, or combinations thereof. The cover 212 has a test-sensor dispensing port 213 extending therethrough and adapted to receive and/or hold a test sensor. The pen meter 200 of the present invention further includes a second cover 214 positioned at a second end 216 of the pen meter 200. FIG. 2b shows the pen meter 200 after the second cover 214 has been removed. Upon removing the second cover 214, a replacement test-sensor cartridge 218 stored within the pen meter 200 is exposed and may be accessed.

According to one embodiment, additional test-sensor cartridges (not shown) may be stacked within the pen meter 200 underneath the replacement cartridge 218 shown in FIG. 2b. It is contemplated that the length L of the pen meter 200 may be extended to accommodate storing such additional replacement cartridges.

Figure 3A:
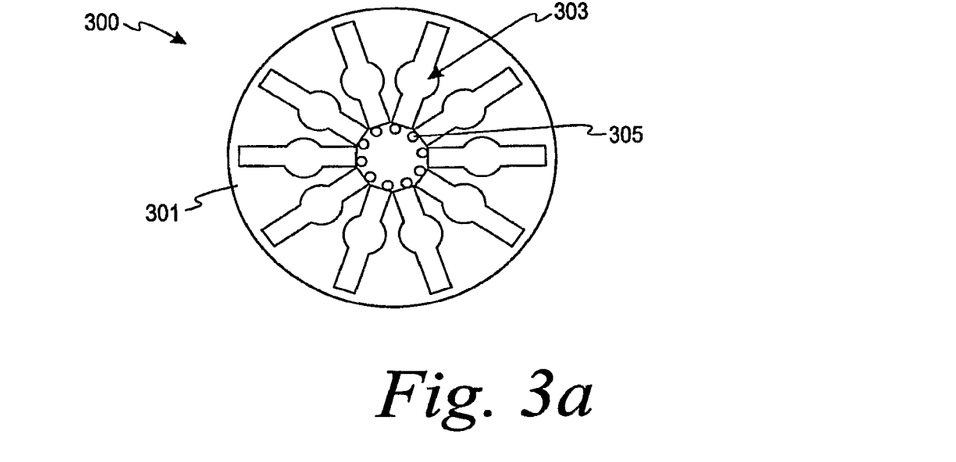
FIG. 3a is a front view of a test-sensor cartridge according to one embodiment.

The meters (e.g., meters 100, 200) of the present invention may be adapted to utilize a compact test-sensor cartridge. One example of a compact cartridge is the cartridge 300 illustrated in FIGS. 1a-c. The cartridge 300 is shown in more detail in FIGS. 3a,b. Referring to FIGS. 3a,b, the cartridge 300 is a generally round drum cartridge having a first generally flat face 301, a second opposing face 307, and a side portion 302 connecting the first and second opposing faces 301, 307. It is contemplated that the cartridge 300 may have other shapes such as, for example, polygonal (e.g., octagon, nonagon, decagon). The cartridge 300 generally has an outer diameter ranging from about 0.25 inches to about 2.0 inches and a length L' ranging from about 0.375 inches to about 2.0 inches. More specifically, the cartridge 300 may have an outer diameter ranging from about 0.50 inches to about 1.0 inches and a length L' ranging from about 0.50 inches to about 1.5 inches. The length L' is generally slightly larger than the length of a test sensor 304 stored within the cartridge 300. The cartridge 300 of the illustrated embodiment includes ten generally uniformly spaced test-sensor cavities 303, each storing a respective one of ten individual test sensors 304. The test-sensor cavities 303 may be interconnected or separate from one another. The test sensors 304 are sealed within the respective test-sensor cavities 303 to assist in preventing or inhibiting the test sensors 304 from being exposed to the atmosphere and/or moisture. The seal may be made of metal foil or other metallic materials or polymeric materials. For example, the seal may be made of a thin polymer with a metal coating for a moisture barrier. Although the test sensors 304 in the embodiment of FIGS. 3a,b have a generally radial layout, it is contemplated that other layouts (e.g., non-radial) may be utilized. The cartridge 300 may further include one or more desiccant compartments 305 for maintaining the test sensors 304 at adequate moisture levels such that accurate testing may be achieved. It is contemplated that the cartridge 300 may include a different number of test sensors 304 and corresponding test-sensor cavities 303 than shown in the illustrated embodiments.

Figure 3B:
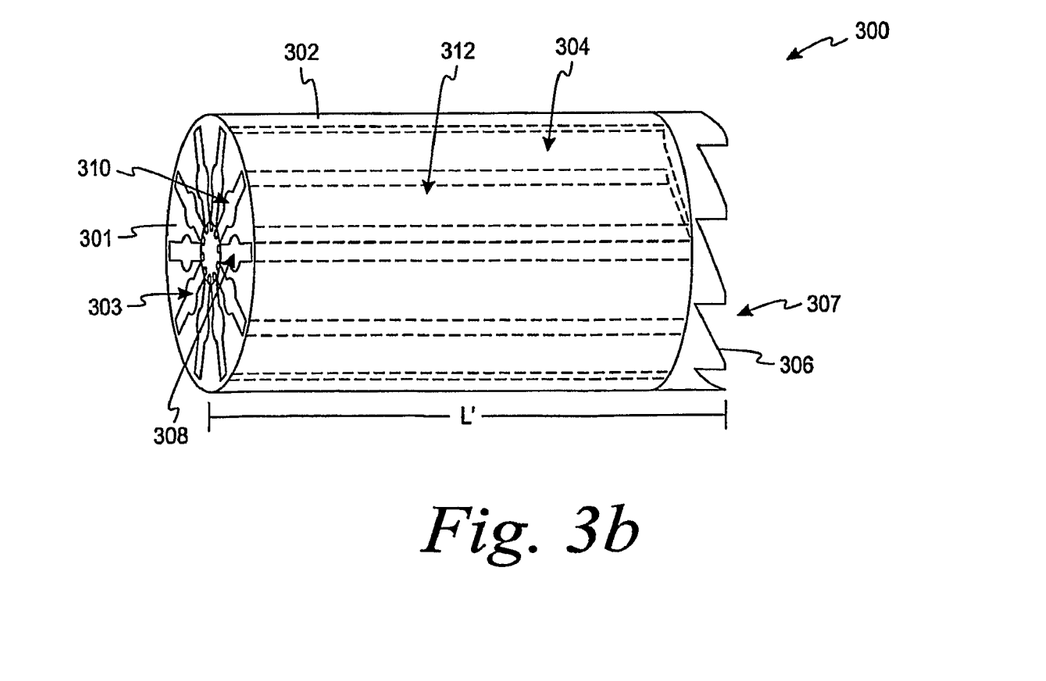

FIG. 3b shows a perspective side view of the cartridge 300 of FIG. 3a. According to the illustrated embodiment, the cartridge 300 includes a plurality of generally uniformly spaced tooth-like notches 306 that is set off at an angle and molded onto the side portion 302 of the cartridge 300. It is comtemplated that the notches 306 may also be positioned along the circumference of the cartridge 300. The number of notches 306 corresponds to the number of test sensors 304 and/or test-sensor cavities 303. Thus, the cartridge 300 of the embodiment of FIGS. 3a,b includes ten notches 306.

Figure 4A:
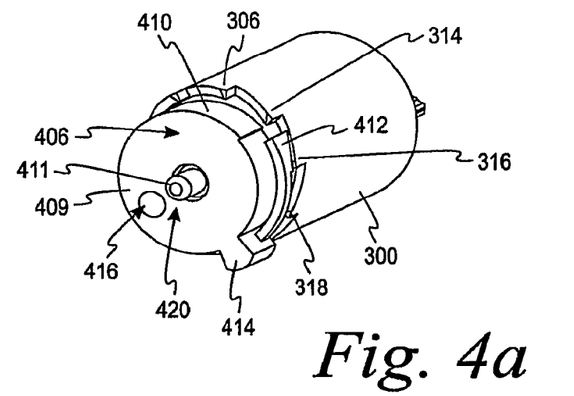
FIG. 4a is a side view of a mechanism for indexing and excising a test sensor from a test-sensor cartridge according to another embodiment of the present invention.
Figure 4B:
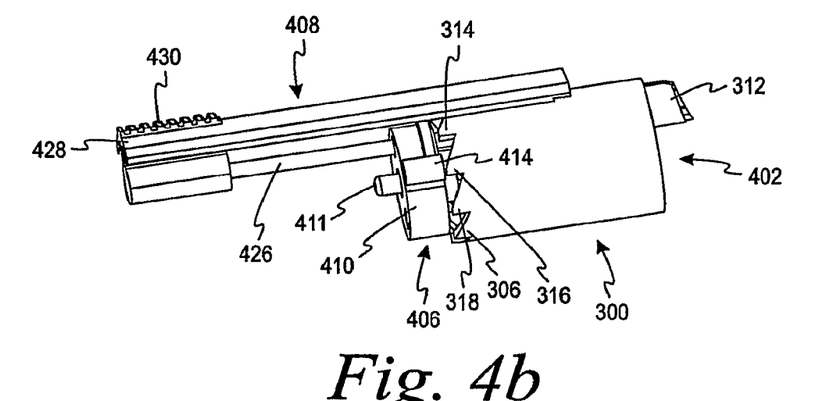
Figure 4C:
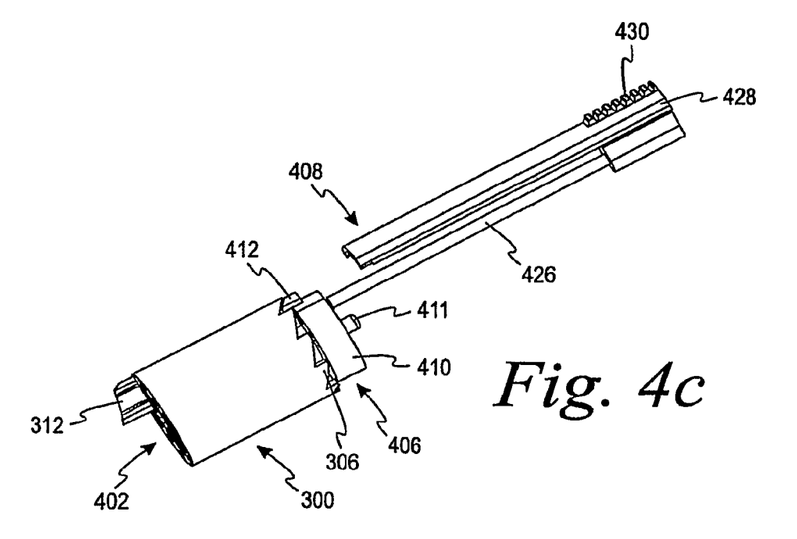
FIG. 4c is another perspective view of the mechanism of FIGS. 4a,b.

According to another embodiment of the present invention, the meters 100, 200 include a mechanism for indexing and/or excising a test sensor from the a test-sensor cartridge. A mechanism 400 according to one embodiment is shown in FIGS. 4a-c. The mechanism 400 of FIGS. 4a-c is shown in combination with the cartridge 300 of FIGS. 3a,b.

FIGS. 1a-c show the mechanism 400 incorporated within the meter 100. FIGS. 2a,b show a similar mechanism 450 incorporated within the pen meter 200. Referring to the embodiment of FIGS. 1a-c, for example, the mechanism 400 is positioned within and substantially parallel to the semicircular end 115 of the meter 100 such that a front end 402 of the mechanism 400 is positioned adjacent to the test-sensor cartridge 300. The mechanism 400 may be similarly positioned within the pen meter 200 of FIGS. 2a,b such that front end 402 (see FIGS. 4b,c) of the mechanism 400 is positioned adjacent to the test-sensor cartridge. It is contemplated that the mechanism 400 of the present invention may also be used in meter types other than those illustrated in FIGS. 1a-c and 2a,b and described above.

Referring to FIGS. 4a-c and 5a,b, the mechanism 400 of the present invention includes an indexer 406 and an excise mechanism 408. The indexer 406 includes a generally round, flat face 409 and a corresponding side portion 410. It is contemplated that the indexer face 406 may have other shapes such as, for example, polygonal (e.g., octagon, nonagon, decagon). The outer diameter of the indexer 406 is generally similar to the outer diameter of the cartridge 300 (e.g., generally ranging from about 0.25 to about 2.0 inches).

The indexer 406 includes a retention pin 411, a flexible pawl 412, a user-accessible tab 414, and an aperture 416 formed therein. The retention pin 411 extends through a second aperture 420 formed generally through the center of the face 409. The retention pin 411 retains the indexer 406 and is generally coupled to a wall within the body of a meter. The flexible pawl 412 is positioned on the side portion 410 near an edge of the indexer face 409. As shown in FIG. 4b, the indexer 406 is positioned relative to the cartridge 300 such that the flexible pawl 412 may fit between any two adjacent notches 306. The flexible pawl 412 is adapted to bend when the indexer 406 is rotated about the retention pin 411 and to spring back into a position between two adjacent notches 306.

Referring back to FIGS. 1a-c, the user-accessible tab 414 is adapted to extend completely through an aperture 120 formed on the body portion 104 of the meter 100. The aperture 120 is shown in FIGS. 1a-c. The aperture 120 is sized such that when the tab 414 is moved from a second end 124 of the aperture 120 to a first end 122 of the aperture 120 in the direction of Arrow A, the indexer 406 is rotated approximately 360/n degrees, where n is the number of test-sensor cavities 303 in the cartridge 300. In the illustrated embodiment, for example, the length of the aperture 120 is sized such that the indexer 406 may be rotated approximately 36 (i.e., 360/10) degrees.

The cartridge 300 may be indexed by rotating the cartridge 300 to replace an empty test-sensor cavity 308 (see FIG. 3b), which is generally aligned with a sensor-dispensing port, with a next test-sensor cavity 310 having a next test sensor 312 therein. The next test sensor 312 is then generally aligned with the dispensing port and may be excised out of the test-sensor cavity 310 and through the dispensing port. To index the cartridge 300 such that the next test sensor 312 may be excised, a user may move the tab 414 through the aperture 120. In the embodiment of FIGS. 1a-c, for example, the tab 414 is moved from the second end 124 to the first end 122 in the direction of Arrow A to index the cartridge 300. As the tab 414 is being moved through the aperture 120, the flexible pawl 412 becomes positioned between a first notch 314 and a second notch 316 (see FIGS. 4a,b) and "catches" the first notch 314 of the cartridge 300. As the user continues to move the tab 414 in the direction of Arrow A, the flexible pawl 412 pushes the first notch 314, thereby rotating the cartridge 300 until the tab 414 reaches the first end 122 of the aperture 120 and may not be moved any further. The notches 306 are positioned on the cartridge 300 such that when the tab 414 reaches the first end 122 of the aperture 120, the cartridge 300 is indexed, and the next test sensor 312 is aligned with the dispensing port 112 and electrical contacts within the meter 100. When the tab 414 reaches the first end 122 of the aperture 120, the indexer 406 is in an index position, as shown in FIG. 5a.

Referring back to FIGS. 4b,c, the excise mechanism 408 includes a push rod 426 and a bar 428. The push rod 426 and the bar 428 are positioned in a generally parallel alignment. At least a portion of the push rod 426 is coupled to at least a portion of the bar 428. At least a portion of the bar 428 is adapted to extend through the body portion 104 of a meter (e.g., meters 100, 200) so that the bar 428 may be accessed by a user (see FIGS. 1a-c and 2a,b) and moved through a lateral path. In the illustrated embodiments of FIGS. 1a-c, for example, a ridged portion 430 of the bar 428 extends through the body portion 104. The ridges may be desirable to provide traction between, for example, a user's finger and the bar 428 to assist in moving the excise mechanism 408. The push rod 426 is adapted to fit through the aperture 416 in the indexer 406.

Figure 5A:
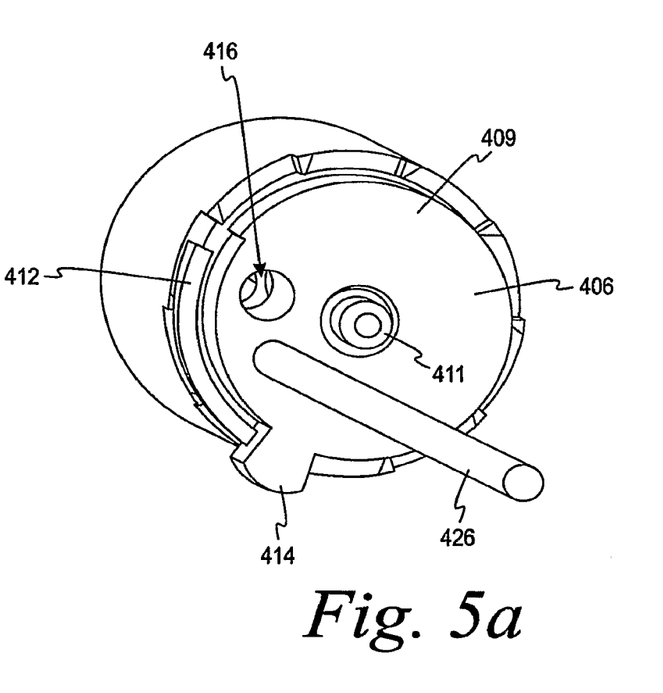
FIG. 5a shows a portion of the mechanism of FIGS. 4a-c in an index position.
Figure 5B:
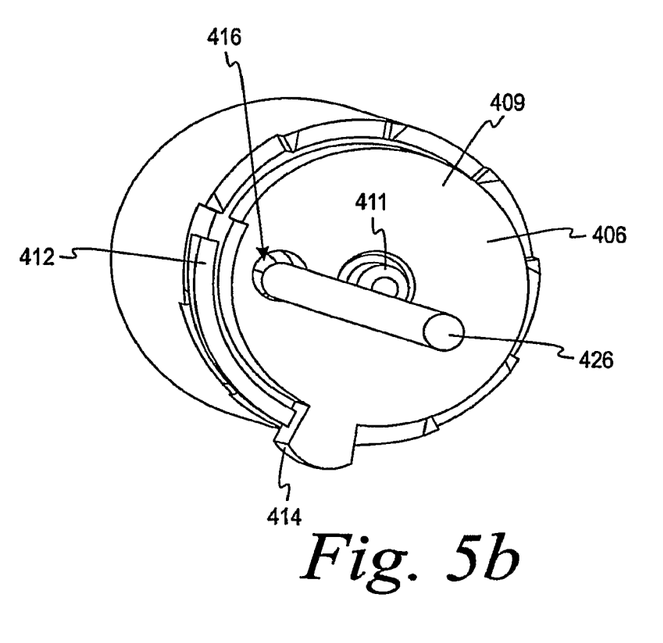
FIG. 5b shows the portion of the mechanism of FIG. 5a in an excise position.

After the cartridge 300 has been indexed, the tab 414 must be moved from the index position of FIG. 5a into to an excise position of FIG. 5b by moving the tab 414 back toward the second end 124 of the aperture 120 in the direction of Arrow B (i.e., the opposite direction of Arrow A) until the tab 414 reaches the second end 124 of the aperture 120. The notches 306 are set off at an angle permitting the cartridge 300 to be rotated in only one direction (i.e., the direction of Arrow A). Thus, as the tab 414 is moved in the direction of Arrow B, the cartridge 300 remains generally stationary, such that the next test sensor 312 and the corresponding test-sensor cavity 310 remain generally aligned with the dispensing port 112. As the tab 414 is moved in the direction of Arrow B, the flexible pawl 412 bends until the indexer 406 is moved a sufficient distance that the flexible pawl 412 may spring back into a position between the next two notches (i.e., the second notch 316 and a third notch 318 of FIGS. 4a,b). When the indexer 406 is in the excise position of FIG. 5b, the test-sensor dispensing port 112, the next test-sensor cavity 310, the next test sensor 312, the aperture 416, and the push rod 426 are all generally aligned.

Once the indexer 406 is in the excise position of FIG. 5b (i.e., the tab 414 is adjacent the second end 124 of the aperture 120), a user may move the bar 428 from a first end 126 toward a second end 128 of a path of the bar 428 in the direction of Arrow C to excise the next test sensor 312. As the bar 428 is moved in the direction of Arrow C, the push rod 426 extends through the aperture 416 in the indexer 406. The push rod 428 then contacts the next test-sensor cavity 310 and may puncture a seal at the end of the test-sensor cavity 310. The push rod 428 then engages the next test sensor 312, pushing the next test sensor 312 in the direction of Arrow C. The next test sensor 312 then may puncture and bursts through a seal at the opposite end of the test-sensor cavity 310. The next test sensor 312 is then excised out of the test-sensor dispensing port 112 into a read position (see, e.g., FIG. 2a), where the next test sensor 312 is aligned with electrical contacts of the meter 100 and an analyte test may be performed.

To test the concentration of an analyte (e.g., glucose) in a body fluid (e.g., blood), a user typically places his or her finger or other area of the body up to a lancet or a lancing device to generate a whole blood sample. Once the user has pierced his or her finger, the user contacts the whole blood sample that has formulated on his or her finger with the excised next test sensor 312. A portion of the blood is generally drawn into a capillary channel of the next test sensor 312 by capillary action. The next test sensor 312 is typically provided with a capillary channel extending from the front or testing end of the sensor to biosensing or reagent material disposed in the next test sensor 312. The biosensing or reagent material is designed to react with the desired analyte to be tested. After a minimum amount of blood is drawn into the next test sensor 312, the blood chemically reacts with the reagent material in the next test sensor 312 such that an electrical signal indicative of the blood glucose level of the sample being tested is supplied and subsequently transmitted to an electrical assembly located within the meter (e.g., meters 100, 200).

According to one embodiment, once the next test sensor 312 is in the read position, the bar 428 reaches the second end 128 of the path and may not be moved any further in the direction of Arrow C. In another embodiment, the excise mechanism 408 may encounter a positive stop at the read position, which is located at some intermediate position between the first end 126 and the second end 128 of the path. It is contemplated that any mechanism suitable for stopping the bar 428 from being moved may be used. For example, a snap mechanism may be used to stop the excise mechanism 408 at the read position. Once the analyte testing has been completed, additional force may be applied to move the bar 428 further in the direction of Arrow C, past the read position, until the used test sensor is ejected out of the dispensing port 112 for disposal. Alternatively, a button (e.g., buttons 108a,b) may be depressed to overcome the positive stop that the excise mechanism 408 encountered at the read position. It is contemplated that other methods of overcoming the positive stop position may also be used.

When the used test strip 312 is ejected, the excise mechanism 408 may be moved in the direction of Arrow D (i.e., the opposite direction of Arrow C) until it contacts the first end 126. If the bar 428 is again moved forward without first indexing the cartridge, a test sensor will not be excised since the test-sensor cavity 310 aligned with the push rod 426 and dispensing port 112 is empty.

Moreover, requiring a user to move the tab 414 back in the direction of Arrow B until the tab 414 contacts the second end 124 of the aperture 120 to excise the next test sensor 312 may also assist in preventing accidental excision of a test sensor, for example, when the indexer 406 is accidentally rotated into the index position of FIG. 5a. A test sensor will not be excised because the push rod 426 is not aligned with the aperture 416. Thus, when a user attempts to move the excise mechanism 408 in the direction of Arrow C, the push rod 426 collides with the face 409 of the indexer 406, and the motion of the excise mechanism 408 is restricted.

It is contemplated that the test-sensor cartridges used with the present invention may include different types of test-sensors. For example, the cartridges may include colorimetric, optical, or electrochemical test sensors.

Alternative Embodiment A

An instrument adapted to determine an analyte concentration of a fluid sample using a test sensor, the instrument comprising:
a display adapted to display information to a user;
a user-interface mechanism adapted to allow the user to interact with the instrument;
a first test-sensor cartridge; and
a body portion including at least a first opening and a second opening formed therein, the first opening being adapted to receive a test sensor from the first test-sensor cartridge, the second opening being adapted to store at least one additional test-sensor cartridge.

Alternative Embodiment B

The instrument of Alternative Embodiment A, wherein the body portion further includes a protective cover, the protective cover being adapted to be removed such that the additional test-sensor cartridge may be accessed.

Alternative Embodiment C

The instrument of Alternative Embodiment A, wherein the at least one additional test-sensor cartridge is a plurality of additional test-sensor cartridges.

Alternative Embodiment D

The instrument of Alternative Embodiment C, wherein the plurality of additional test-sensor cartridges is stacked.

Alternative Embodiment E

A mechanism adapted to index and excise a test sensor from a test-sensor cartridge comprising:
an indexer comprising an indexer face, a retention pin, a flexible pawl, and a user-accessible tab, the retention pin extending through a first aperture formed generally through the center of the indexer face, the indexer being adapted to be rotated in a first direction and a second direction about the retention pin, the flexible pawl positioned near an edge of the indexer face, the flexible pawl being adapted to assist in rotating the test-sensor cartridge, the indexer face forming a second aperture therein, the second aperture adapted to be generally aligned with the test sensor; and
an excise mechanism comprising a push rod adapted to extend through the second aperture and a bar coupled with and generally parallel to the push rod.

Alternative Embodiment F

The mechanism of Alternative Embodiment E, wherein the cartridge is adapted to be rotated and indexed when the indexer is rotated in a first direction, and
wherein the cartridge is adapted to remain substantially stationary when the indexer is rotated in a second direction generally opposite to the first direction.

Alternative Embodiment G

The mechanism of Alternative Embodiment F, wherein the indexer is rotated by moving the tab.

Alternative Embodiment H

An analyte-testing instrument adapted to determine the concentration of at least one analyte in a fluid, the analyte-testing instrument comprising:
a display adapted to display information to a user;
a user-interface mechanism adapted to allow the user to interact with the instrument;
a body portion including at least one opening formed therein, the at least one opening being adapted to receive a test sensor;
an indexer positioned within the body portion, the indexer comprising an indexer face, a retention pin, a flexible pawl, and a user-accessible tab, the retention pin extending through a first aperture formed generally through the center of the indexer face, the indexer being adapted to be rotated in a first direction and a second direction about the retention pin, the flexible pawl positioned near an edge of the indexer face, the flexible pawl being adapted to assist in rotating the test-sensor cartridge, the indexer face forming a second aperture therein, the second aperture adapted to be generally aligned with the test sensor; and
an excise mechanism positioned within the body portion, the excise mechanism comprising a push rod adapted to extend through the second aperture and a bar coupled with and generally parallel to the push rod.

Alternative Embodiment I

The mechanism of Alternative Embodiment H, wherein the instrument further comprises a test-sensor cartridge comprising a first face, a second opposing face, and a side portion connecting the first and second opposing faces, the first face forming a plurality of test-sensor cavities that is generally uniformly positioned therethrough, and a plurality of generally uniformly spaced notches positioned on an end of the cartridge opposite the cartridge face, the number of notches corresponding to the number of cavities, wherein the flexible pawl is adapted to fit between any two adjacent notches.

Alternative Embodiment J

The assembly of Alternative Embodiment I, wherein the analyte-testing instrument further comprises an aperture in the body portion, the tab being adapted to extend therethrough,
wherein the length of the aperture in the body portion is sized such that the moving the tab from a first end of the aperture to a second end of the aperture rotates the indexer approximately 360/n degrees, where n is the number of test-sensor cavities.

Alternative Embodiment K

The assembly of Alternative Embodiment J, wherein the analyte-testing instrument further comprises a second aperture in the body portion, at least a portion of the bar being adapted to extend therethrough such that the bar may be moved in a lateral direction to excise the test sensor.

Alternative Process L

A method of indexing and excising a test sensor from a test-sensor cartridge, the method comprising the acts of:
providing a test-sensor cartridge comprising a first face, a second opposing face, and a side portion connecting the first and second opposing faces, the first face forming a plurality of test-sensor cavities that is generally uniformly positioned therethrough, and a plurality of generally uniformly spaced notches positioned on an end of the cartridge opposite the cartridge face, the number of notches corresponding to the number of cavities;
providing an indexer comprising an indexer face, a retention pin extending through a first aperture formed generally through the center of the indexer face, a second aperture formed on the indexer face, a flexible pawl positioned near an edge of the indexer face, the flexible pawl being adapted to assist in rotating the test-sensor cartridge, and a user-accessible tab;
providing an excise mechanism comprising a push rod adapted to extend through the second aperture and a bar coupled with and generally parallel to the push rod;
rotating the indexer in a first direction about the retention pin such that the flexible pawl is positioned between a first notch and an adjacent second notch, wherein the notches are set off at an angle such that rotating the indexer in a first direction, but not in a second generally opposite direction, likewise rotates the cartridge;
rotating the indexer in the second direction such that the flexible pawl is positioned between the second notch and an adjacent third notch and the second aperture is generally aligned with a first test-sensor cavity;
moving the excise mechanism in a lateral direction such that the push rod extends through the second aperture and through a first end of the first test-sensor cavity; and
continuing to move the excise mechanism in the lateral direction until the first test sensor is excised through the second end of the first test-sensor cavity into a read position.

Alternative Process M

The method of Alternative Process L, further comprising the act of performing an analyte-testing procedure.

Alternative Process N

The method of Alternative Process M, further comprising the act of continuing to move the excise mechanism in the lateral direction such that the test-sensor is ejected.

Alternative Process O

The method of Alternative Process L, further comprising the acts of providing an analyte-testing instrument comprising a display adapted to display information to a user, a user-interface mechanism adapted to allow the user to interact with the instrument, and a body portion including at least one opening formed therein, the at least one opening being adapted to receive the test sensor.

Alternative Process P

The method of Alternative Process O, wherein the test sensor is aligned with electrical contacts within the analyte-testing instrument when the test sensor is in the read position.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention as defined by the appended claims.

The invention claimed is:

1. An instrument configured to determine a concentration of at least one analyte in a fluid sample using a test sensor, the instrument comprising:
a body portion having a display configured to display information to a user and a user-interface mechanism configured to allow a user to interact with the instrument;
a first compartment positioned at a first end of the body portion, the first compartment including a first test-sensor cartridge, the first test-sensor cartridge including a plurality of test sensors, the first test-sensor cartridge being removable from the first compartment;
a second compartment positioned at a second, opposing end of the body portion such that the first and second compartments are separated from one another by a mechanism at least partially within the body portion, the second compartment including a plurality of stacked test-sensor cartridges, each of the plurality of stacked test-sensor cartridges including a plurality of test sensors, each of the plurality of stacked test-sensor cartridges being detached from and not in contact with the first test-sensor cartridge, each of the plurality of stacked test-sensor cartridges being removable from the second compartment; and
an opening formed at the first end of the body portion, the opening being configured to receive a test sensor from the first test-sensor cartridge.

2. The instrument of claim 1, further comprising a cover configured to be removed such that the plurality of stacked test-sensor cartridges may be accessed.

3. The instrument of claim 1, wherein the instrument has a generally elongated shape.

4. The instrument of claim 1, wherein the first test-sensor cartridge is aligned with the plurality of stacked test-sensor cartridges.

5. The instrument of claim 1, wherein the mechanism is for indexing or indexing and excising a test sensor from the test-sensor cartridge.

6. The instrument of claim 1, wherein each of the plurality of test sensors includes a capillary channel extending from a testing end of each of the plurality of test sensors and a reagent material configured to react with the at least one analyte.

7. An instrument configured to determine a concentration of at least one analyte in a fluid sample using a test sensor, the instrument comprising:
a body portion having a generally elongated shape, the body portion having an opening formed at a first end;
a first compartment positioned at the first end of the body portion, the first compartment including a first test-sensor cartridge, the first test-sensor cartridge including a plurality of test sensors, the opening being configured to receive a single one of the test sensors from the first test-sensor cartridge; and
a second compartment positioned at a second, opposing end of the body portion such that the first and second compartments are separated from one another by a mechanism at least partially within the body portion, the second compartment including more than one stacked test-sensor cartridge, each of the more than one stacked test-sensor cartridge including a plurality of test sensors, each of the more than one stacked test-sensor cartridge being generally parallel to the first test-sensor cartridge.

8. The instrument of claim 7, further comprising a display configured to display information to a user.

9. The instrument of claim 7, further comprising a user-interface mechanism configured to allow a user to interact with the instrument.

10. The instrument of claim 7, further comprising a cover configured to be removed such that the more than one stacked test-sensor cartridge may be accessed.

11. The instrument of claim 7, wherein the mechanism is for indexing or indexing and excising a test sensor from the test-sensor cartridge.

12. The instrument of claim 7, wherein each of the plurality of test sensors includes a capillary channel extending from a testing end of each of the plurality of test sensors and a reagent material configured to react with the at least one analyte.

* * * * *